United States Patent [19]

Huhn et al.

[11] Patent Number: 5,109,125
[45] Date of Patent: Apr. 28, 1992

[54] PROCESS FOR PURIFYING NUCLEOSIDE-5'-DIPHOSPHATES

[75] Inventors: George F. Huhn, Newark; James H. Jensen, Wilmington, both of Del.

[73] Assignee: Du Pont Merck Pharmaceutical Company, Wilmington, Del.

[21] Appl. No.: 335,122

[22] Filed: Apr. 7, 1989

[51] Int. Cl.$^5$ .................... C07H 19/10; C07H 19/20
[52] U.S. Cl. ........................ 536/28; 536/27; 536/29; 210/656; 210/635
[58] Field of Search ............ 536/27, 28, 29; 210/656, 635

[56] References Cited

U.S. PATENT DOCUMENTS

| | | | |
|---|---|---|---|
| 3,337,529 | 8/1967 | Laufer | 544/266 |
| 3,509,128 | 4/1970 | Fujimoto et al. | 536/28 |
| 3,534,017 | 10/1970 | Fujimoto et al. | 536/28 |
| 3,787,392 | 1/1974 | Bergmeyer et al. | 536/28 |
| 3,803,125 | 4/1974 | Bergmeyer et al. | 536/28 |
| 4,430,496 | 2/1984 | Abbott | 536/27 |

OTHER PUBLICATIONS

Duolite Ion Exchange Manual, Diamond Shamrock Chemical Co., 1969, cover page, pp. VII, VIII, 96–105, and 162–171.

Michaelson, *Biochem. Biophys.* ACTA, 1964, 91:1–13.

Moffatt & Corona, *J. Amer. Chem. Soc.*, 1961, 83:649–658.

*Primary Examiner*—Johnnie R. Brown
*Assistant Examiner*—Gary L. Kunz
*Attorney, Agent, or Firm*—Don M. Kerr; Gildo E. Fato

[57] ABSTRACT

This invention is a process for purifying nucleoside-5'-diphosphates containing substituents other than primary amines (hereinafter designated as NDPs) from complex mixtures by contacting the aqueous solution mixture with a strongly basic ion exchange resin in the chloride form, eluting certain absorbed impurities with an alkali metal salt solution, converting the column to the hydroxide form by contacting the resin with an alkali metal hydroxide solution such that the effluent becomes basic, and eluting absorbed NDP with a weakly acidic alkali metal salt solution such that solutions of highly pure NDP are obtained in basic effluent fractions. The new process is particularly valuable for purification of NDPs directly from chemical synthesis reaction media.

10 Claims, No Drawings

PROCESS FOR PURIFYING NUCLEOSIDE-5'-DIPHOSPHATES

BACKGROUND OF INVENTION

Nucleoside-5'-diphosphates containing purine or pyrimidine heterocycles are useful intermediates in the synthesis of biologically active compounds such as oligoribonucleotides. Nucleoside-5'-diphosphates are sources of energy and phosphoric acid in cellular metabolic processes, and are important in the biosynthesis of nucleic acids.

Ion exchange chromatography is commonly used to purify a variety of materials, including pharmaceuticals, on a manufacturing scale. There is a wide amount of literature available on various processes (*Duolite* ® *Ion-Exchange Manual*, Diamond Shamrock Chemical Company, 1969).

Nucleoside-5'-diphosphates are commonly synthesized by reacting an activated 5'-nucleotide, such as a nucleoside-5'-monophosphoramidate or 1-diphenyl-2-(5'-nucleoside)diphosphate, with multiple equivalents of a tertiary amine salt of phosphoric acid in an anhydrous organic solvent (Michelson, *Biochem. Biophys. Acta* (1964) 91:1-13; Moffat and Khorana, *J. Am. Chem. Soc.* (1961) 83:649-658; U.S. Pat. No. 3,534,017 (1970)). Formation of by-products during the synthesis such as 1,2-di(5'-nucleoside)diphosphate (NPPN) and 1,3-di(5'-nucleoside)triphosphate (NPPPN) usually occur from the reaction of the activated 5'-nucleotide with 5'-nucleotide and nucleoside-5'-diphosphate, respectively.

NDPs are usually purified directly from the reaction media by ion exchange chromatography. The reaction masses are sometimes treated with activated carbon to remove organic solvents and inorganic phosphate before ion exchange chromatography. In other methods, organic solvents are removed by vacuum distillation and the residue reconstituted with water before ion exchange purification. For large-scale NDP manufacturing, it is desirable to purify NDPs directly from the reaction mass by ion exchange chromatography without the additional carbon treatment or vacuum distillation.

The ion exchange purification schemes most often used involve absorbing the nucleoside-5'-phosphate derivatives onto a column of strongly basic ion exchange resin containing quaternary polymer-bound trimethylamine sites (Type 1 resins) or quaternary polymer-bound dimethylmonoethanolamine sites (Type 2 resins) in the chloride form. The compounds are then individually eluted with dilute acid or dilute acid and salt solutions. The purification of uridine-5'-diphosphate and uridine-5'-triphosphate by such a method is described by Fujimoto and Teranishi in U.S. Pat. No. 3,509,128 (1970).

We have found that ion exchange systems similar to these were unable to separate certain nucleoside-5'-diphosphates, such as those containing purine or pyrimidine heterocycles without a primary amine constituent, from other phosphorylated impurities present in the chemical reaction matrix, such as NPPN. In all of the ion exchange chromatography systems we tried using acid and/or alkali metal salt solutions, NPPN co-eluted with NDP.

Experiments to test relative absorption of these compounds on the strongly basic ion exchange resin showed that NPPN was selectively retained over NDP by the strongly basic ion exchange resin in basic solutions, but not selectively retained in acidic solutions. Therefore, it appeared advantageous to develop a method to elute IDP under basic conditions.

Strongly basic ion exchange resins have a low affinity for the hydroxide anion; therefore, most ion exchange purifications using strongly basic ion exchange resins are performed using acidic eluents. Although hydroxide ion will exchange with chloride ion on strongly basic ion exchange resin, hydroxide ion, even in high concentration, is not strong enough to exchange with nucleoside-5'-phosphate derivatives on the resin. For this reason, the hydroxide ion has not been used in ion exchange chromatography purifications of phosphate derivatives using strongly basic resins.

SUMMARY AND DESCRIPTION OF INVENTION

We have discovered a procedure for obtaining solutions of highly pure NDPs by selectively eluting the NDPs from strongly basic ion exchange resin under basic conditions, a procedure heretofore unknown by those skilled in the art.

An additional advantage to our invention is that the purified NDPs obtained in the slightly basic solutions are not subject to acid hydrolysis (U.S. Pat. No. 3,509,128) as they are in the usual acidic elution schemes.

This new procedure is particularly useful for purifying NDPs directly from reaction media of a chemical synthesis.

According to the present invention, we provide a process for purifying certain NDPs in an aqueous solution from inorganic phosphate, phosphorylated nucleoside derivatives, and organic solvents and bases contained therein. The process involves the following steps:

1) The aqueous solution containing impure NDP is passed through a column of strongly basic ion exchange resin in the chloride form such that the NDP is absorbed by the strongly basic resin.

2) The strongly basic resin is preferably washed with water or alkali metal salt solution to elute organic solvents and other impurities not absorbed by the strongly basic resin.

3) Weakly absorbed impurities, such as inorganic phosphate and 5'-nucleotide, are eluted from the strongly basic resin by means of an alkali metal salt solution.

4) The strongly basic resin is converted from the chloride form to the hydroxide form by contact with an aqueous alkali metal hydroxide solution until the said column effluent pH becomes greater than 11.

5) The strongly basic resin is preferably washed with water or alkali metal salt solution to displace the said alkali metal hydroxide solution from the interstitial voids in the column.

6) The absorbed NDP is eluted from the strongly basic resin by means of a weakly acidic solution of an alkali metal salt and an inorganic and/or organic acid such that highly purified solutions of said NDP are collected before the effluent pH drops below 8.5.

The pH of the aqueous NDP impurity matrix may be adjusted to between 3 and 10 to improve absorption of the phosphorylated compounds on the strongly basic resin; however, satisfactory results are also obtained without the pH adjustment.

It is necessary to use a slightly acidic alkali metal salt solution to elute NDP because NDP will not elute if the alkali metal salt solution is basic. Too much acidity is not desirable because it causes the effluent pH to become acidic before a good yield of highly pure NDP solutions can be obtained.

Residual NDP, NPPN, NTP, and NPPPN absorbed on the column are eluted as the column is regenerated to the chloride form with a hydrogen chloride and/or alkali metal chloride solution.

The purified NDP can be isolated from the ion exchange effluent streams by conventional means known to those skilled in the art such as concentration by distillation, ion exchange chromatography, or reverse osmosis followed by precipitation or spray drying.

PREFERRED EMBODIMENT

The invention is now described in greater detail by the following working examples. These examples are meant to illustrate the invention, but by no means limit the scope of the invention.

EXAMPLE 1

168.6 g of a reaction mass containing inosine-5'-diphosphate (IDP) (34.6 mM), inosine-5'-monophosphate (IMP) (3.3 mM), 1,2-di(5'-inosine)diphosphate (IPPI) (0.69 mM), 1,3-di(5'-inosine)triphosphate (IPPPI) (1.4 mM), inosine-5'-triphosphate (ITP) (0.44 mM), and inorganic phosphate (approximately 125 mM), in N,N-dimethylacetamide with small amounts of morpholine and N,N'-dicyclohexyl-4-morpholinocarboxamidine was diluted with water to 1020 g, clarified, and adjusted to pH 6 with 2.4 mL 50% sodium hydroxide. The solution was then passed through a 60×2.5 cm$^2$ glass column containing a 50 cm bed of commercially available (Dow Chemical Co.) Dowex ® 1×8 strongly basic anion exchange resin in the chloride form at 23 mL per minute. The effluent was monitored by an in-line UV detector at 254 nm and an in-line pH probe. The resin was washed with water until the unretained materials had eluted, and the effluent UV absorbance had become sufficiently low. The flow rate was then increased to 29 to 30 mL per minute, and a solution of sodium chloride (0.12M) was passed through the column to elute inorganic phosphate and IMP. Aqueous sodium hydroxide (0.06M) was then passed through the column as the main IMP peak began to elute, and was continued until IMP ceased to elute and the pH of the effluent increased sharply to greater than 12. The resin was washed with water until the pH decreased to 9.65. A solution of sodium chloride (0.20M) and hydrogen chloride (0.01M) was passed through the column, and fractions containing purified IDP were collected when the effluent UV absorbance began to rise, and collection continued until the pH decreased to 8.5. A total of 1903 g of solution was collected and combined, and HPLC analysis of this solution assayed 26 mM IDP of 99.21 HPLC area percent purity. The recovery of purified IDP was 75%. The remaining fractions collected after the pH dropped below 8.15 contained between 4.8 and 29.1 HPLC area percent IPPI. The column was then washed with HCl (2.0M) until the absorbance had become sufficiently low. HPLC analysis of the 2.0M HCl wash showed IPPPI, ITP, and residual IMP, IDP, and IPPI.

EXAMPLE 2

23 mL of a reaction mass containing uridine-5'-diphosphate (UDP) (3.3 mM) in N,N-dimethylacetamide was assayed by HPLC and shown to have the following composition of phosphorylated uridine derivatives by HPLC area percent: uridine-5'-phosphoromorpholidate (UMP-PM) 2.08%, uridine-5'-monophosphate and 1,2-di(5'-uridine)diphosphate (UMP and UPPU respectively) 7.28% (not resolved well on chromatogram), UDP 87.81%, 1,3-di(5'-uridine)triphosphate (UPPPU) 2.25%, and uridine-5'-triphosphate (UTP) 0.58%. The solution also contained inorganic phosphate (approximately 20 mM) and small amounts of morpholine, triethylamine, and N,N'-dicyclohexyl-4-morpholinocarboxamidine. The mass was diluted with water (115 ml), adjusted to pH 9 with sodium hydroxide, and clarified. The solution was passed at 11 mL per minute through a 25×1.5 glass column packed with Dowex ® 1×8 strongly basic ion exchange resin in the chloride form (a commercially available resin from the Dow Chemical Co.). The effluent was monitored by an in-line UV detector (254 nm) and in-line pH probe. The resin was then rinsed with water until the absorbance was sufficiently low, and a solution of sodium chloride (0.075M) passed through the column to elute UMP-PM, inorganic phosphate, and UMP. After most of the UMP had eluted, a solution of sodium hydroxide (0.05M) was passed through the column until the effluent pH rose to 12. The column was then rinsed with water until the effluent pH dropped below 10. A solution of sodium chloride (0.15M) and hydrogen chloride (0.002M) was passed through the column, and fractions containing purified UDP were collected when the effluent had strong UV absorption, and continued until the pH had dropped below 9. These fractions (420 mL total) contained 2.76 mM UDP of greater than 99.4 HPLC area percent purity. The recovery of purified UDP was 84%. The fractions collected after the pH dropped below 9 contained between 0.2 to 6 HPLC area percent UPPU.

What we claim is:

1. A process for purifying inosine and uridine 5'-diphosphates, from an impurity matrix which comprises a) passing an aqueous solution of the matrix through a cationic ion exchange resin in the chloride form, b) eluting any organic solvents, small amounts of dissolved non-ionic organic impurities which are not absorbed by the resin and any weakly absorbed ionic impurities with an alkali metal salt solution, c) passing an aqueous alkali metal hydroxide solution through the column to convert the column resin to the hydroxide form such that the effluent pH becomes greater than 11, and d) eluting purified solutions of inosine 5'-diphosphate or uridine 5'-diphosphate with an acidic solution of an alkali metal salt such that the pH of effluent containing purified inosine 5'-diphosphate or uridine 5'-diphosphate remains above 8.5 during the period during which the greatest portion of purified inosine 5'-diphosphate or uridine 5'-diphosphate nucleoside solution is collected.

2. The process of claim 1 wherein the strongly basic ion exchange resin is a crosslinked polystyrene resin containing trimethylamine or dimethylethanolamine quaternary ammonium exchangers.

3. The process of claim 2 wherein the alkali metal salt solution contains a salt selected from the group consisting of sodium chloride, lithium chloride, potassium chloride.

4. The process of claim 3 wherein the concentration of the alkali metal salt solution is 0.01 to 1.0N.

5. The process of claim 4 wherein the alkali metal hydroxide solution contains a salt selected from the group consisting of sodium hydroxide, lithium hydroxide, potassium hydroxide.

6. The process of claim 5 wherein the concentration of the alkali metal hydroxide solution is 0.01 to 0.10N.

7. The process of claim 6 wherein the concentration of the alkali metal salt solution is 0.05 to 0.5N alkali metal salt.

8. The process of claim 7 wherein the alkali metal salt solution contains an acid from the group consisting of hydrochloric acid, sulfuric acid, nitric acid, formic acid, acetic acid.

9. The process of claim 8 wherein the concentration of the alkali metal salt solution is 0.001 to 0.05N acid.

10. A process for purifying inosine and uridine 5'-diphosphates from a matrix containing them which comprises a) passing an aqueous solution of the matrix through a column of cationic ion exchange resin in the chloride form, b) eluting any impurities with an alkali metal salt solution, the salt selected from the group consisting of sodium chloride, lithium chloride and potassium chloride, the salt solution being 0.01 to 1.0N, c) passing an aqueous alkali metal hydroxide solution containing a salt selected from the group consisting of sodium hydroxide, lithium hydroxide and potassium hydroxide, the solution being from 0.1 to 0.10N, through the column to convert the column resin to the hydroxide form such that the effluent pH becomes greater than 11, and d) eluting purified solutions of inosine or uridine-5'-diphosphate with an acidic solution of an alkali metal salt such that the pH of effluent containing purified inosine or uridine-5'-diphosphate remains above 8.5 during the period during which the greatest portion of purified inosine or uridine-5'-diphosphate solution is collected.

* * * * *